(12) United States Patent
Dorneanu (10) Patent No.: US 10,426,980 B2
(45) Date of Patent: Oct. 1, 2019

(54) SMART SPRAY FOAM RESPIRATOR MASK

(71) Applicant: Daniel Dumitru Dorneanu, Charleston, SC (US)

(72) Inventor: Daniel Dumitru Dorneanu, Charleston, SC (US)

(73) Assignee: Daniel D. Dorneanu, Charleston, SC (US)

( * ) Notice: Subject to any disclaimer, the term of this patent is extended or adjusted under 35 U.S.C. 154(b) by 0 days.

(21) Appl. No.: 15/905,312

(22) Filed: Feb. 26, 2018

(65) Prior Publication Data

US 2018/0247245 A1    Aug. 30, 2018

Related U.S. Application Data

(60) Provisional application No. 62/463,854, filed on Feb. 27, 2017, provisional application No. 62/474,657, (Continued)

(51) Int. Cl.
| | |
|---|---|
| *A62B 18/08* | (2006.01) |
| *G02B 27/01* | (2006.01) |
| *G06Q 10/06* | (2012.01) |
| *A61B 5/00* | (2006.01) |
| *A62B 9/00* | (2006.01) |

(Continued)

(52) U.S. Cl.
CPC ............ *A62B 18/08* (2013.01); *A61B 5/0022* (2013.01); *A61B 5/6823* (2013.01); *A62B 7/00* (2013.01); *A62B 9/006* (2013.01); *A62B 18/02* (2013.01); *G02B 27/01* (2013.01);
(Continued)

(58) Field of Classification Search
CPC ... H04M 1/72533; F04D 15/00–15/029; F04D 27/00–27/0292; G05D 7/00–7/0694; G05D 11/00–11/16; G05D 16/00–16/2093; G05D 23/00–24/02;
(Continued)

(56) References Cited

U.S. PATENT DOCUMENTS 5,764,203 A * 6/1998 Holmlund .............. A62B 9/006
  345/8
7,038,639 B1 * 5/2006 Olstad .................... B63C 11/12
  345/8

(Continued)

*Primary Examiner* — Gennadiy Tsvey
(74) *Attorney, Agent, or Firm* — Daniel D. Dorneanu; PSF R&D Labs (57) ABSTRACT

SPF (spray polyurethane foam) insulation applied in a commercial or residential building is an amazing but costly construction product. One reason is that application of SPF insulation requires large investment capital equipment and a specialized crew for each job. The work is further made difficult because interface with the complex plural component machine (proportioner) is not possible from the location where the work is being performed (where the applicator and spray gun are.) We worked to solve this problem by designing a wireless system to communicate with the proportioner at the point of use (POU) where we are spraying. We designed the system to interface with all proportioner brands used by contractors keeping the user interface and majority of components standard for all. The applicator can now efficiently interact with his equipment and make smart strategic decisions on-demand. Using our system, the average applicator can improve his productivity by 13-17% per job.

6 Claims, 10 Drawing Sheets

Related U.S. Application Data filed on Mar. 22, 2017, provisional application No. 62/629,040, filed on Feb. 11, 2018.

(51) Int. Cl.

| | | |
|---|---|---|
| *A62B 18/02* | (2006.01) | |
| *A62B 7/00* | (2006.01) | |
| *H04M 1/725* | (2006.01) | |
| *H04W 84/12* | (2009.01) | |

(52) U.S. Cl.
CPC .... *G06Q 10/06316* (2013.01); *A61B 2503/20* (2013.01); *H04M 1/72533* (2013.01); *H04W 84/12* (2013.01)

(58) Field of Classification Search
CPC .. G02B 27/01; A62B 7/00; A62B 7/10; A62B 9/00–006; A62B 18/00–08
See application file for complete search history.

(56) References Cited

U.S. PATENT DOCUMENTS

| | | | | |
|---|---|---|---|---|
| 7,178,931 B1* | 2/2007 | Murphy | ............... | A62B 18/08 2/410 |
| 7,398,097 B2* | 7/2008 | Parkulo | ............... | G08B 25/016 340/501 |
| 7,926,118 B2* | 4/2011 | Becker | ............... | A61F 9/067 2/8.2 |
| 9,895,267 B2* | 2/2018 | Cole | ............... | A61F 9/06 |
| 2003/0058100 A1* | 3/2003 | Jumpertz | ............... | A42B 3/0433 340/540 |
| 2005/0016540 A1* | 1/2005 | Jumpertz | ............... | A62B 9/04 128/205.22 |
| 2007/0181129 A1* | 8/2007 | Mattinson | ............... | A62B 9/006 128/206.21 |
| 2008/0023002 A1* | 1/2008 | Guelzow | ............... | A42B 3/042 128/201.24 |
| 2008/0094935 A1* | 4/2008 | Newton | ............... | A01C 23/042 366/132 |
| 2008/0185001 A1* | 8/2008 | McWilliams | ............... | B63C 11/12 128/204.21 |
| 2010/0308991 A1* | 12/2010 | Adams | ............... | A62B 18/08 340/539.12 |
| 2012/0152253 A1* | 6/2012 | Leuschner | ............... | A62B 9/006 128/204.26 |
| 2013/0112195 A1* | 5/2013 | Smith | ............... | G02B 27/017 128/202.13 |
| 2014/0071294 A1* | 3/2014 | Lavoie | ............... | H04N 5/2251 348/164 |
| 2014/0084025 A1* | 3/2014 | Tix | ............... | F04B 17/03 222/135 |
| 2014/0163749 A1* | 6/2014 | Phillips | ............... | G05D 7/0676 700/283 |
| 2015/0142491 A1* | 5/2015 | Webb | ............... | G06Q 10/063114 705/7.15 |
| 2015/0378371 A1* | 12/2015 | Lange | ............... | H04Q 9/00 700/282 |
| 2016/0030775 A1* | 2/2016 | Bryntesen | ............... | A62B 9/006 128/202.13 |
| 2016/0319826 A1* | 11/2016 | Shanks | ............... | H04L 67/125 |
| 2016/0381717 A1* | 12/2016 | Sunagar | ............... | H04B 17/318 370/328 |
| 2017/0067214 A1* | 3/2017 | Harrison, Jr. | ............... | E01C 19/21 |
| 2017/0080262 A1* | 3/2017 | Freres | ............... | A62B 9/04 |
| 2017/0080346 A1* | 3/2017 | Abbas | ............... | A63F 13/825 |
| 2017/0132799 A1* | 5/2017 | Yajko | ............... | G06T 7/90 |
| 2018/0109740 A1* | 4/2018 | Pickett | ............... | H04N 5/33 |
| 2018/0218535 A1* | 8/2018 | Ceylan | ............... | G06T 7/13 |
| 2019/0033594 A1* | 1/2019 | Patil | ............... | A62B 18/08 |
| 2019/0056258 A1* | 2/2019 | Gelada Camps | ...... | G01F 23/292 |
| 2019/0118008 A1* | 4/2019 | Thompson | ............... | A62B 9/006 |

* cited by examiner

| | | | | JobSight SKY Rig Log: Truck 8750 | | | | | | |
|---|---|---|---|---|---|---|---|---|---|---|
| | | | | September 6 2017 3:12pm | | | | | | |
| Live: | Pa: 1425 | Pb: 1310 | Ta: 128 | Tb: 128 | Th: 128 | Va: 32 | Vb: 27 | Fa: 2.91 | R: 2.1 | Y: 9.1 |
| Live: | * | * | O | * | * | Pc: 135 | Tc: 160 | Fb: 2.93 | Tix: 72 | Tbx: 74 |
| | | OC | CC | HRS | Depth | Difficulty | | | | |
| | Target: | 60 | 0 | 8 | 3.5 | 5 | | OSE: | 72.56% | |

| Goal | Time | Cycles | Pdelta | Q-ratio | Yield | Q-sight | MC | Notes |
|---|---|---|---|---|---|---|---|---|
| 0 | 7:05 | | | | | | | |
| 277 | 8:05 | 233 | 150-175 | 2.2 - 2.4 | NA | 3.6 | 105 | gun side seal gunk on A |
| 555 | 9:05 | 504 | 200-250 | 2.4 - 2.6 | NA | 3.9 | 104 | catching up |
| 832 | 10:05 | 745 | 250-300 | 2.6 - 2.8 | NA | 3.3 | 99 | |
| 1109 | 11:05 | 1012 | 300-350 | 2.8 - 3.0 | 8.11 | 3.5 | 98 | stopped to replace oring |
| 1247 | 12:05 | 1234 | 150-175 | 2.0-2.1 | 9.3 | 3.7 | 99 | lunch |
| 1525 | 1:05 | 1523 | 150-175 | 2.0-2.1 | NA | 3.8 | 104 | jose kicking butt...... |
| 1801 | 2:05 | 1820 | 150-175 | 2.0-2.1 | NA | 3.5 | 107 | |
| 2078 | 3:05 | 2090 | 150-175 | 2.0-2.1 | NA | 3.6 | 110 | catching up |

Figure 13

| | | | | JobSight SKY Fleet Status | | | | | | |
|---|---|---|---|---|---|---|---|---|---|---|
| | | | | September 6 2017 10:12am | | | | | | |
| Rig | Pdelta | Goal | Th | Cycles | C 2 Goal | Q-ratio | Yield | MC | OSE% | Status |
| Truck 6121A | 100-125 | 1200 | 128 | 435 | -17 | 2.1 | 107 | 107 | 73 | Spraying |
| Truck 6121B | 120-150 | 1125 | 132 | 245 | -75 | 3.2 | 105 | 115 | 56 | Spraying |
| Truck 2383A | 170-350 | 870 | 131 | 410 | 89 | 1.5 | 112 | 98 | 84 | Spraying |
| Truck 2384A | 100-150 | 1378 | 90 | 345 | 35 | na | 50 | 87 | 62 | Idle |
| Truck 2384B | 12/15 | 789 | 98 | 7 | -350 | na | na | na | 7 | Down |
| Truck 2387A | na/na | na/na | na | na | na | na | na | na | na | Offline |
| Truck 2387B | 100-200 | 1030 | 127 | 333 | 23 | 2.3 | na | 96 | 85 | Spraying |

Figure 14

SMART SPRAY FOAM RESPIRATOR MASK

This application claims the benefit of U.S. Application No. 62/463,854 filed Feb. 27, 2017 titled Smart Spray Foam Respirator Mask, the benefit of U.S. Application No. 62/474, 657 filed Mar. 22, 2017 titled Spray Foam Insulation Assisted Spray Technology and the benefit of U.S. Application No. 62/629,040 filed Feb. 11, 2018 titled Smart Spray Foam Depth Sensor. The contents of which are hereby incorporated by reference.

TECHNICAL FIELD

Polyurethane Spray Foam Insulation

BACKGROUND

Figure 1:
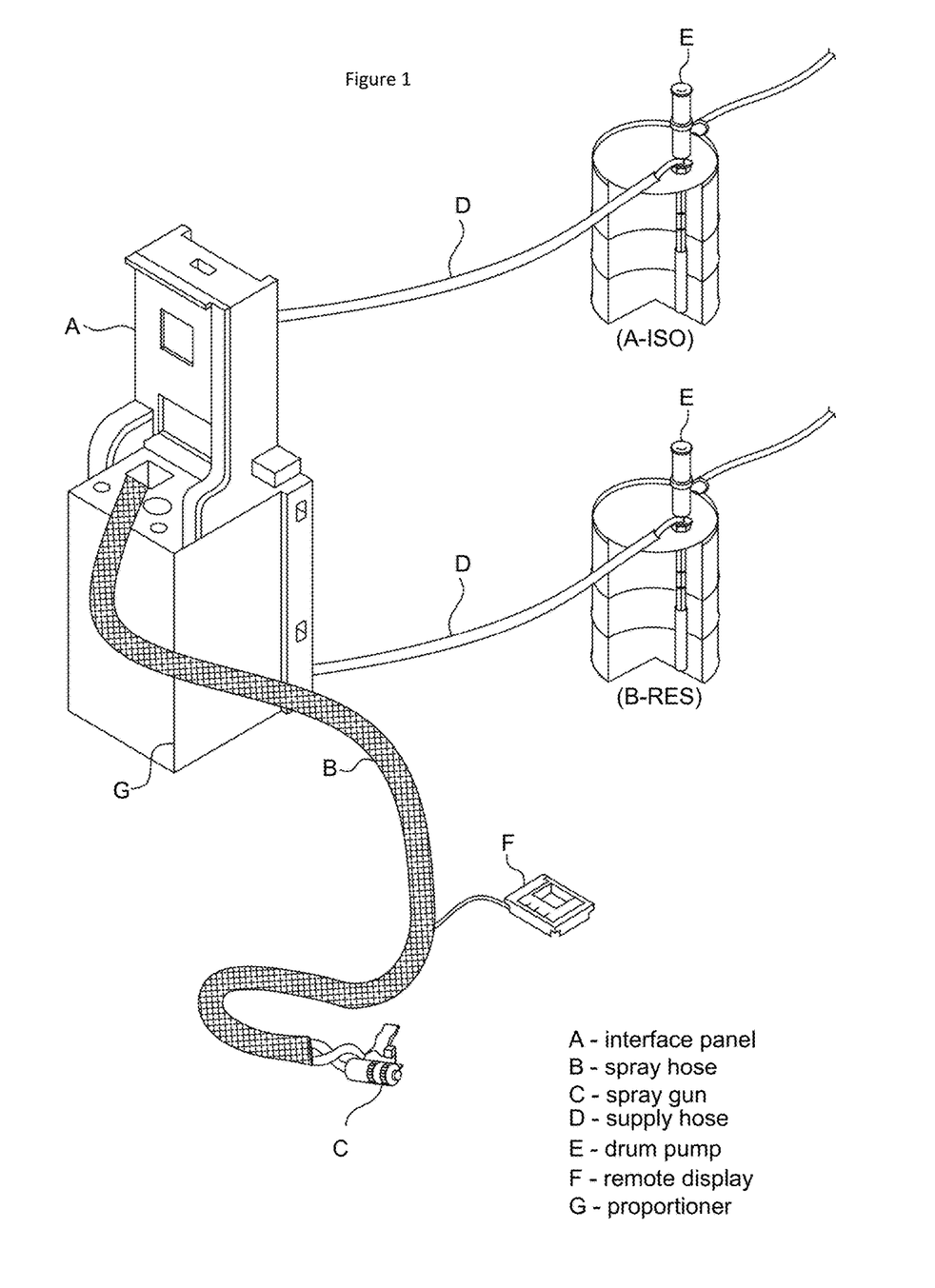
FIG. 1 shows typical main components of a spray foam rig. Person spraying is at the end of the hose (B) and spraying with gun (C).
Figure 2:
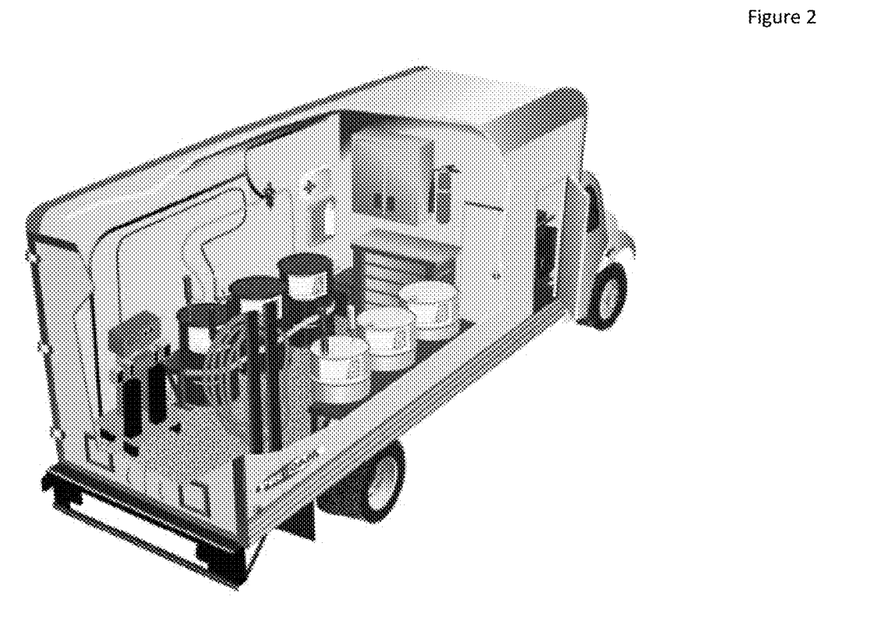
FIG. 2 shows the components from FIG. 1 inside of a truck which is how many contractors operate. The truck parks next to the building to be sprayed. Spray hose is then rolled out inside the building to the areas to be sprayed (attic, walls, crawlspace, etc.)
Figure 3:
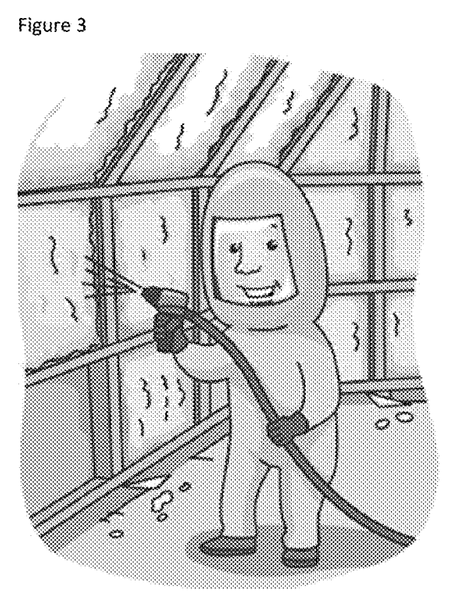
FIG. 3 shows the point of use (POU) area where we spray.

In our spray foam insulation company we often work in extreme environments (130 F-150 F with limited air supply) and 100-300 feet away from the spray proportioner (FIG. 1: part A) in the truck FIG. 2. The proportioner is a machine used to heat and pressurize the two (2) chemicals required for the exothermic reaction process which produces SPF (spray polyurethane foam) insulation. The two (2) chemicals travel through the spray hose (FIG. 1: part B) to the spray gun (FIG. 1: part C) where the sprayer is performing the work. When spraying, we wear a fresh air respirator mask (FIG. 5) to protect the sprayer from harmful fumes produced during the reaction process between chemical A and chemical B mixed at the spray gun. The only way in the past for us to view and/or modify proportioner parameters (temperatures, pressures, etc.) is to stop spraying and walk back to the truck. Other alternative is to radio to a person in the truck who can interact with the proportioner and relay the information back to the sprayer on the radio. This process is very inefficient and time consuming. Our employees saw the need and productivity advantage to be gained if the sprayer can access the equipment controls remotely and wirelessly at the point of use (POU) FIG. 3. We thus went to work and developed a heads-up-display unit FIG. 6 (with control) built inside our respirator mask. For safety reasons we incorporated visual readings of the sprayers physiological vitals (heat rate, breathing rate, core temperatures, etc.) coming from sensors attached on the sprayer's torso FIG. 9.

PRIOR ART

On the market today (as of Feb. 27, 2017 provisional filing,) there are multiple products allowing monitoring and display of a person's physiological vitals. There is also a tethered (corded) display panel (FIG. 1: part F) which operates with one single specific spray foam proportioner. Problem—There is not a wireless device allowing the sprayer at the point of use (POU) FIG. 3 to view and modify any mark/brand of proportioner equipment parameters. There is nothing which also monitors and/or displays the sprayers physiological vitals in the same system. And there is nothing which allows the above functions performed from inside the sprayer's respirator mask.

SUMMARY OF THE INVENTION

Figure 4:
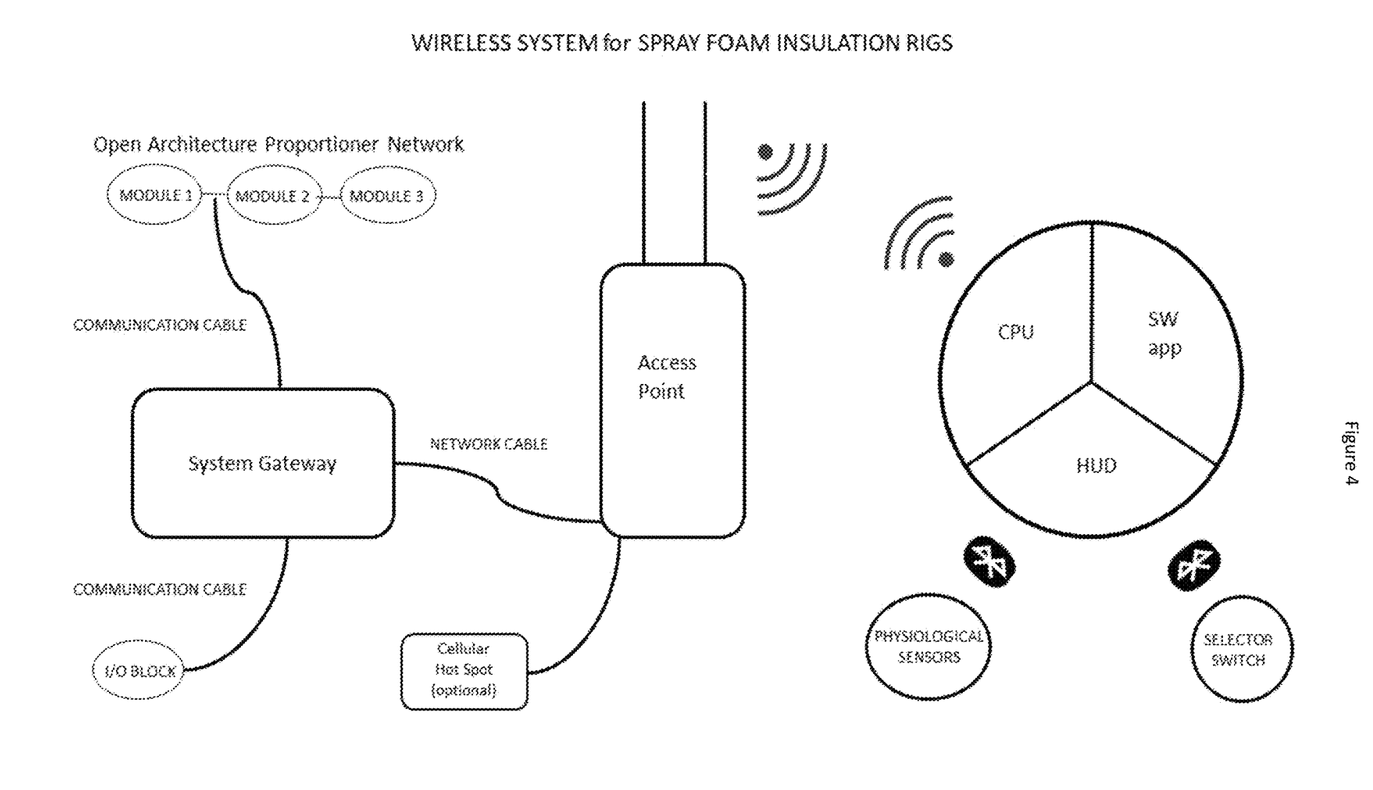
FIG. 4 shows a diagram of the wireless system components.
Figure 5:
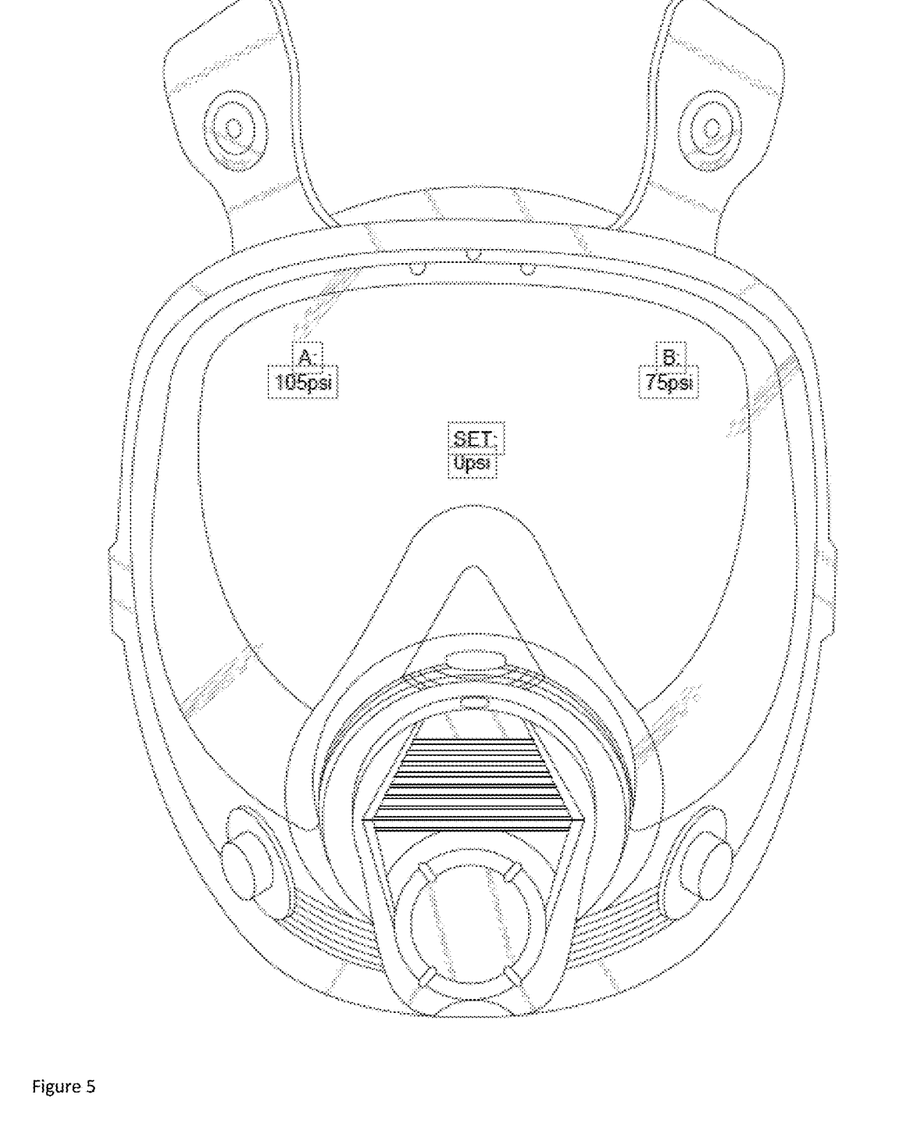
FIG. 5 shows a schematic of the smart spray foam respirator mask.
Figure 6:
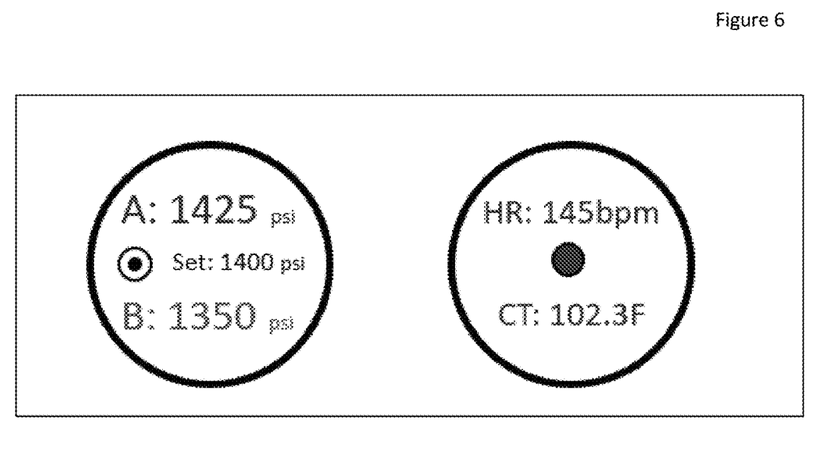
FIG. 6 shows a closer detail of the HUD display.
Figure 9:
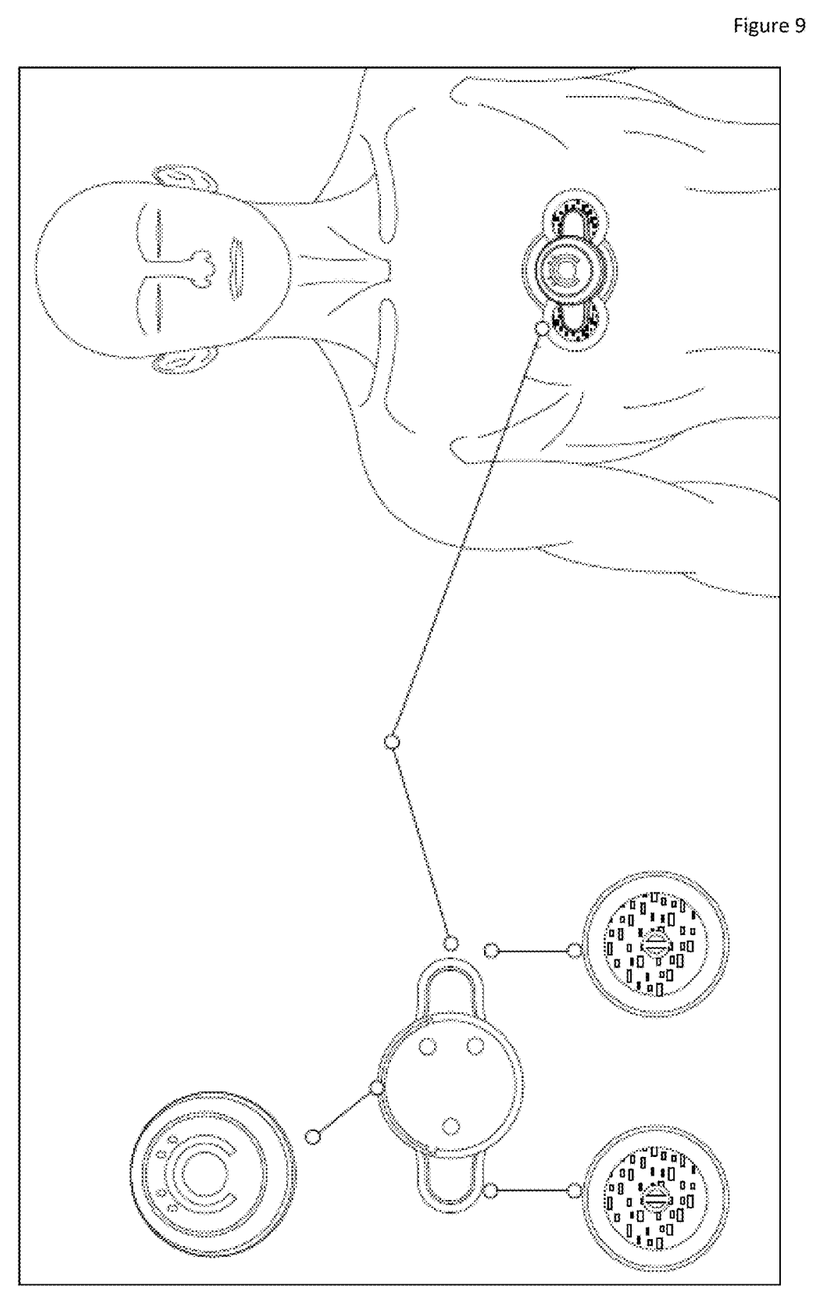
FIG. 9 shows an example of a physiological vitals monitoring system.

Our company built a wireless smart heads-up-display system (FIG. 4) which can be incorporated into any full-face respirator mask (FIG. 5). The HUD displays specific proportioner parameters (temperatures, pressures, etc.). The HUD also displays the sprayer's physiological vitals (using data received from sensors attached to the person's torso.) FIG. 9. The HUD system allows the sprayer to view and modify the proportioner parameters wirelessly from 300 feet away. Solution—Our product innovation allows for remote wireless viewing and modification of proportioner parameters and for remote monitoring of the sprayer's physiological vitals. The combined data is then viewed on an OLED (organic light emitting diode) display. Our software application allows the above listed wireless functionality to be done from a smart phone, or a tablet, or a smart watch or from inside the smart spray foam respirator mask.

DETAILED DESCRIPTION OF INVENTION

Figure 10:
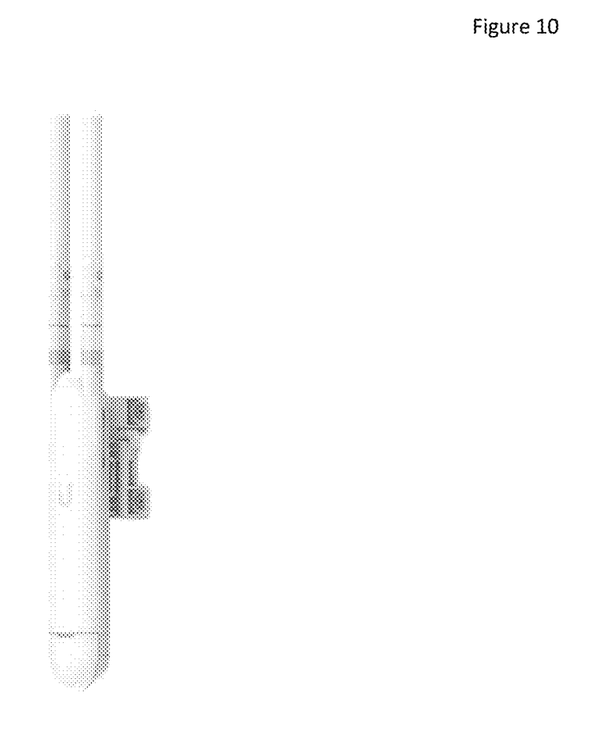
FIG. 10 shows an outdoor access point (AP.)

The wireless smart HUD system (FIG. 4) consists of an android based controller connected to an OLED micro display. The android controller runs a software application which communicates using WIFI (IEEE 802.11) to a wireless outdoor Access Point (AP) FIG. 10 mounted on exterior of the Rig. The AP is connected to a gateway using a network cable. The gateway is connected to the proportioner network using a communication cable. The processor running the proportioner application inside the smart mask also runs the physiological vitals software which receives data from the vitals sensors attached to the sprayers torso (heart rate, breathing rate, core temperature, etc.).

Figure 7:
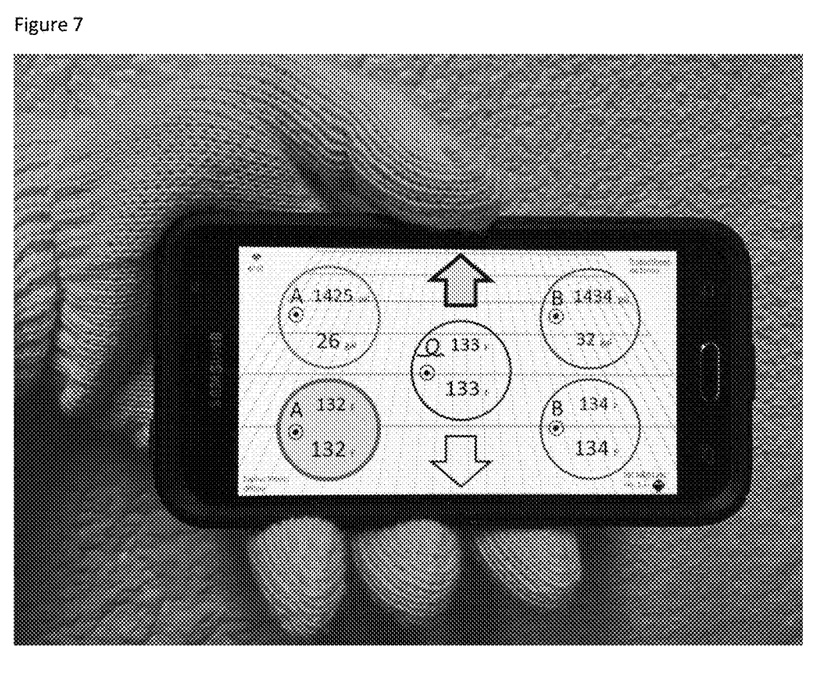
FIG. 7 shows a schematic of the software application running on a smart phone.

The software application running on Android communicates with the gateway using WIFI 802.11 technology to display proportioner parameter data on the OLED display (FIG. 7). These display parameters include temperature A, temperature B, temperature Hose, pressure A, pressure B, cycle count, heater A on/off status, heater B on/off status, heater Hose on/off status, pump on/off status, flow rate A, flow rate B.

The software application communicates with the physiological sensors using Bluetooth technology to display sprayer physiological vitals data on the OLED display. This data includes heart rate, breathing rate, core temperature and Stress level.

Figure 11:
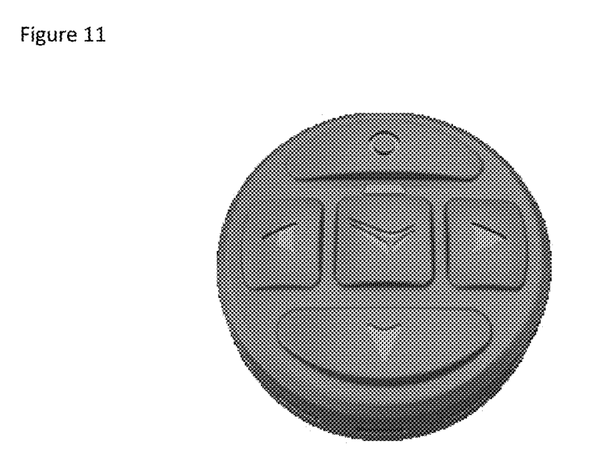
FIG. 11 shows a selector switch used to interface with the smart mask HUD.

The software application communicates with a selector switch (FIG. 11) allowing the user to interact and modify specific proportioner parameters displayed on the OLED display. The modifiable parameters include temperature setpoint A, temperature setpoint B, temperature setpoint Hose, pressure setpoint, heater A on/off, heater B on/off, heater Hose on/off, pump on/off.

Mask Option:

We chose the OLED emissive micro display because it does not require a backlight and so is thinner (more compact) and more efficient than LCD displays (which do require a white backlight). OLED communication with the android processor is done using serial peripheral interface (SPI.) The OLED allows for an improved image quality when used with a projection application. The mask option operator interaction uses a selector switch communicating over Bluetooth Low Energy. The switch scrolls through parameters which can be modified and initiates the modification.

Figure 8:
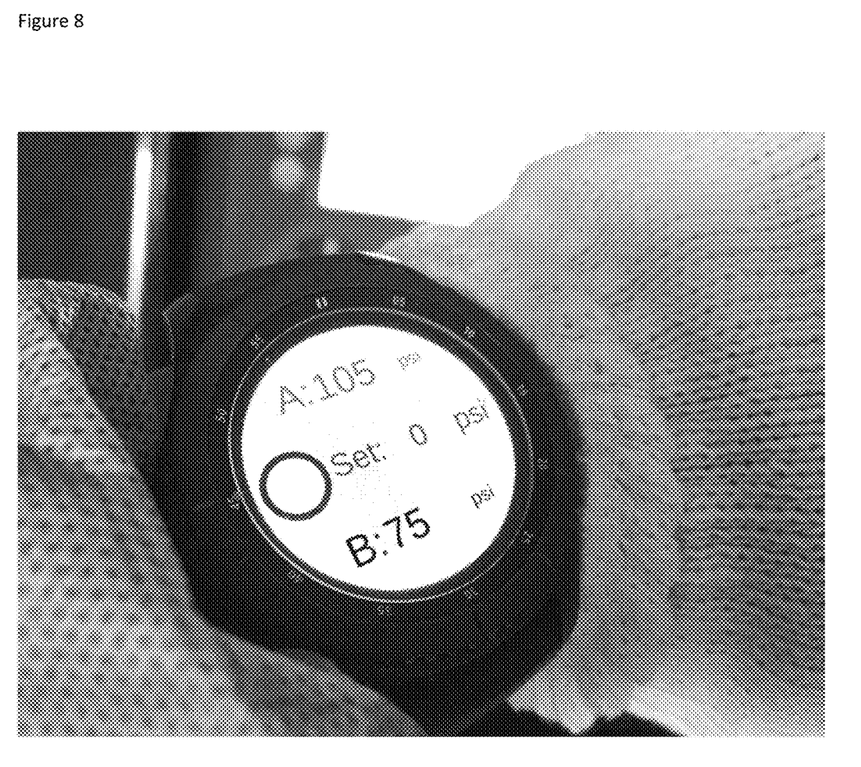
FIG. 8 shows a schematic of the software application running on a wearable device.

Wearable Option:

As a more cost-efficient option the system makes possible the use of a wearable device (FIG. 8) with WIFI capability, such as a smart watch. The preferred smart watch has a touchscreen but also makes use of a rotating bezel to facilitate sprayer interaction when wearing gloves. The rotating bezel allows for changing screens and for modification of a parameter (such as temperature setpoint A), simply by rotating the bezel.

Processor:

Development of the software application was done using Unity 3D, a versatile development platform allowing final application to be run on multiple operating systems. Unity engine allowed for interface with existing devices without need for an existing API or SDK (for example wearables new on the market.) Unity also allowed for fast processing loops even when running on less powerful (1 GHZ) and lower RAM processor (768 Mb.)

Gateway:

The communication gateway transmits and receives serial messages on the open architecture proportioner network. The gateway is the only device in the system which can vary between proportioner brand families based on network communication protocol. Messages received are translated into the displayed parameters. Modifiable parameters are translated into messages sent on the proportioner network. The gateway can also communicate to an I/O block connected directly to the proportioner analog transducers, thermocouples, flow meters or temperature controllers.

Access Point:

The above functionality is possible remotely and wirelessly from up to 600' away from proportioner using IEEE 802.11 (WIFI) technology. The access point (AP) FIG. 10 connection strength is maximized by locating the AP on the exterior of the rig. Using 2.4 GHZ bandwidth allows for maximum speed and range penetrating through solid objects such as walls and floors which is required when operator is spraying inside a building. The AP used also allows for weather ruggedness in extreme environments and possible contact with tree branches when driving.

Figure 12:
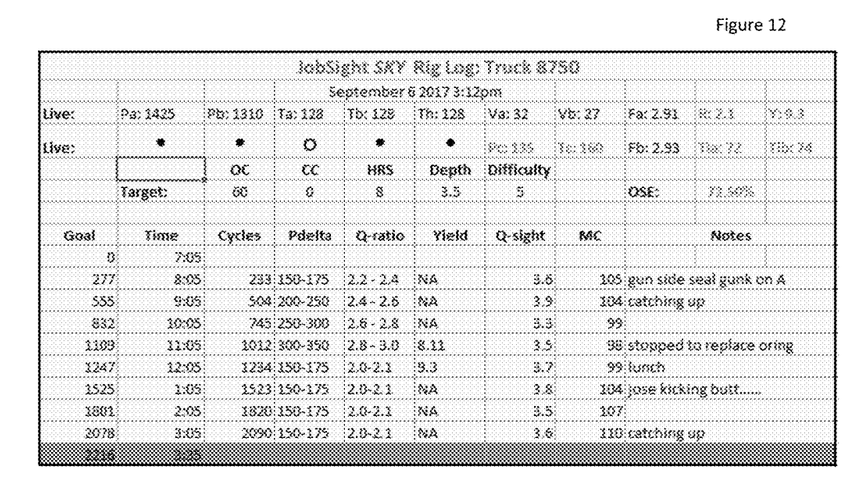
FIG. 12 shows a log of the sprayer's workday with historical parameter data.
Figure 13:
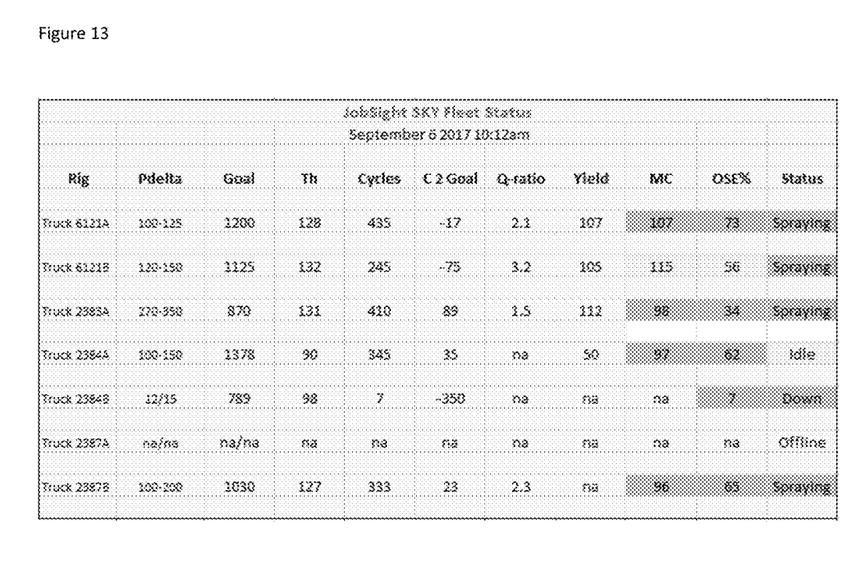
FIG. 13 shows a cloud database log with historic and live parameter data of multiple rigs spraying.
Figure 14:
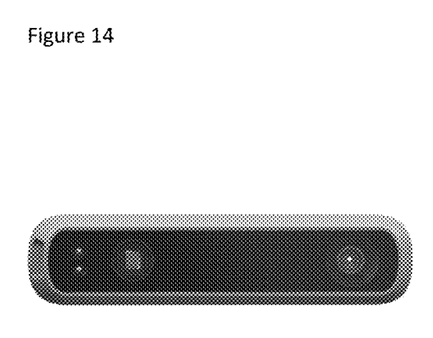
FIG. 14 shows an optical depth sensor used to scan a three (3) dimensional surface for purpose of recording a three (3) dimensional map of an object.

Functionality:

The software application allows for additional smart functionality such as mapping a progression log (FIG. 12) of the sprayer's workday (as described in provisional U.S. Application No. 62/474,657: Spray Foam Insulation Assisted Spray Technology.) The log tracks the sprayers hour by hour job progress and populates historical parameter data along the way such as showing material Ratio variance each hour. The sprayer can also make use of the log to see if he is ahead or behind schedule at any point during the work day. At the end of the work day, the job log can serve as a historical summary of that specific job at that specific worksite. The work day log can also be uploaded to a cloud database via an optional cellular hot spot connected to the AP. With such option, a fleet of rigs can be monitored via a tablet connecting to the cloud service (FIG. 13.) Other optional functionality is to make use of a smart spray foam depth sensor (FIG. 14) (as described in provisional U.S. application 62/629,040: Smart Spray Foam Depth Sensor.) The optical depth sensor data is interpreted by the software application and displayed on the HUD.

Similar functionality can be achieved using a microdisplay, a see-thru display (wave guide technology) or by projection (image is reflected from the respirator mask face shield onto the sprayer's retina.) Similar functionality can be achieved when interfacing with proportioners which make use of other open architecture communication protocols such as RS-485, CAN Open, ModBus, DeviceNet, Profibus, etc. by making use of corresponding gateway. Similar functionality can be achieved when interfacing with proportioners which make only partial use or do not use a communication network by making use of a gateway which connects to an I/O block connected directly to the proportioner analog transducers, thermocouples, flow meters or temperature controllers. Similar functionality can be achieved using other communication protocols with the physiological sensors, with the gateway, with the selector switch and with the access point.

One Example of Intended Use:

Intended use is for the sprayer on each spray foam rig to wear the smart spray foam respirator mask when applying spray foam polyurethane insulation in residential and commercial buildings. Empowered with the parameter data at the point of use (POU) the sprayer can quickly optimize the proportioner parameters and make smart strategic decisions regarding his workday. Similarly, as a more cost-efficient option, the sprayer can use the smart phone app downloaded to his phone to monitor and control the proportioner.

The invention claimed is:

1. A local wireless communication system comprising of:
   a) an electronic processor and a graphical user interface display allowing for viewing and modification of operating parameters of a fluid applicator system capable of pumping two or more fluids;
   b) a software application allowing said viewing and modification to be done from inside a smart spray foam respirator mask using an internal projection display and a selector switch communicating using personal area network technology;
   c) a communication gateway to interface with corresponding proportioner network protocol and/or directly to analog transducers, thermocouples, flow meters and temperature controllers;
   d) an access point providing a wireless local area network connection based on IEEE 802.11 technology; and
   e) an interface to an optical depth sensor located within the smart spray foam respirator mask and used to scan a three-dimensional surface to record a three-dimensional map of a sprayed polyurethane foam surface.

2. The local wireless communication system according to claim 1 with added functionality of a physiological vitals monitoring system whereby sprayer vitals and calculated performance levels are visible inside the smart spray foam respirator mask.

3. The local wireless communication system according to claim 1 where said software application can run on multiple operating systems.

4. The local wireless communication system according to claim 1 where the access point is connected to a cloud database via a cellular hot spot for upload capability of historic and live parameter data.

5. The local wireless communication system according to claim 1 where the smart spray foam respirator mask includes local 2-way radio communication with other crew members on site using personal area network technology.

6. The local wireless communication system according to claim 1 where the smart spray foam respirator mask includes smart functionality of mapping a progression log of a sprayer's workday.

* * * * *